(12) United States Patent
Eberhard et al.

(10) Patent No.: US 10,532,169 B2
(45) Date of Patent: Jan. 14, 2020

(54) SMALL, LOW-NOISE SIDE CHANNEL COMPRESSOR, IN PARTICULAR FOR DEVICES IN VENTILATION THERAPY

(71) Applicant: TNI MEDICAL AG, Würzburg (DE)

(72) Inventors: Dietmar Eberhard, Kenzingen (DE); Ewald Anger, Eibelstadt (DE)

(73) Assignee: TNI MEDICAL AG, Würzburg (DE)

(*) Notice: Subject to any disclaimer, the term of this patent is extended or adjusted under 35 U.S.C. 154(b) by 743 days.

(21) Appl. No.: 14/648,127

(22) PCT Filed: Nov. 19, 2013

(86) PCT No.: PCT/EP2013/074134
§ 371 (c)(1),
(2) Date: May 28, 2015

(87) PCT Pub. No.: WO2014/082892
PCT Pub. Date: Jun. 5, 2014

(65) Prior Publication Data
US 2015/0297850 A1  Oct. 22, 2015

(30) Foreign Application Priority Data
Nov. 29, 2012  (DE) ........................ 10 2012 023 347

(51) Int. Cl.
*A61M 16/00*  (2006.01)
(52) U.S. Cl.
CPC ..... *A61M 16/0063* (2014.02); *A61M 2205/10* (2013.01); *A61M 2205/42* (2013.01)

(58) Field of Classification Search
CPC .......... A61M 16/0057; A61M 16/0063; A61M 16/0066; A61M 16/0069; A61M 2205/10; A61M 2205/42; A62B 7/00–002; A62M 18/006; F04D 5/002; F04D 29/188; F04D 29/26; F04D 29/266; F04D 29/284; F04D 29/666; F04D 23/008
See application file for complete search history.

(56) References Cited

U.S. PATENT DOCUMENTS

| 3,951,567 A |   | 4/1976 | Rohs |
| 5,395,784 A | * | 3/1995 | Lu .................... H01L 27/10808 |
|             |   |        | 257/E21.651 |
| 5,487,639 A | * | 1/1996 | Asabuki ................ F04D 23/008 |
|             |   |        | 415/55.1 |

(Continued)

FOREIGN PATENT DOCUMENTS

| DE | 38 23 514 A1 | 1/1990 |
| DE | 92 07 883 U1 | 9/1992 |

(Continued)

*Primary Examiner* — Jennifer M Deichl
(74) *Attorney, Agent, or Firm* — McGlew and Tuttle, P.C.

(57) ABSTRACT

The invention relates to a small, low-noise side channel compressor for producing a defined volumetric flow, such as is needed in particular for devices for ventilation therapy. This is achieved by means of a new type of shape of the blade chambers (24) in the impeller (12) and the blade chamber walls (29), which separate the blade chambers and become thicker toward the circumference of the impeller, supported by a high-speed drive and a large number of blade chambers (24) at a small impeller diameter.

20 Claims, 6 Drawing Sheets

(56) References Cited

U.S. PATENT DOCUMENTS

| | | | | |
|---|---|---|---|---|
| 5,498,124 | A * | 3/1996 | Ito | F04D 5/002 415/55.1 |
| 6,224,323 | B1 * | 5/2001 | Murase | F02M 37/08 415/55.1 |
| 6,425,732 | B1 * | 7/2002 | Rouse | F04D 23/008 29/407.05 |
| 6,890,144 | B2 * | 5/2005 | Yu | F02M 37/048 415/119 |
| 2003/0118438 | A1 | 6/2003 | Usui et al. | |
| 2004/0016432 | A1 | 1/2004 | Genger et al. | |
| 2004/0177849 | A1 * | 9/2004 | Del Bon | A61M 11/06 128/203.12 |
| 2007/0231121 | A1 | 10/2007 | Baecke et al. | |
| 2012/0057995 | A1 * | 3/2012 | Schofield | F04D 5/005 417/65 |
| 2012/0301267 | A1 * | 11/2012 | Baecke | A61M 16/0057 415/1 |

FOREIGN PATENT DOCUMENTS

| | | |
|---|---|---|
| DE | 196 49 529 A1 | 6/1998 |
| DE | 199 13 950 A1 | 9/2000 |
| DE | 101 05 383 A1 | 8/2002 |
| DE | 20 2004 019 071 U1 | 5/2006 |
| DE | 10 2005 040 305 A1 | 3/2007 |
| DE | 10 2006 024 839 A1 | 11/2007 |
| DE | 10 2006 041 557 A1 | 3/2008 |
| EP | 1 519 050 A2 | 3/2005 |
| EP | 1 703 136 B1 | 4/2009 |
| EP | 2 128 200 A1 | 12/2009 |
| EP | 2 207 967 B1 | 5/2011 |
| JP | S57-206795 A | 12/1982 |
| JP | 2002-339 889 A | 11/2002 |
| KR | 10-0190424 B1 | 6/1999 |
| WO | 02/16776 A1 | 2/2002 |
| WO | 02/062413 A2 | 8/2002 |
| WO | 20061039894 A2 | 4/2006 |
| WO | 2010/133866 A1 | 11/2010 |

* cited by examiner

Section A-A

Section B-B   *Fig. 9*

SMALL, LOW-NOISE SIDE CHANNEL COMPRESSOR, IN PARTICULAR FOR DEVICES IN VENTILATION THERAPY

Side channel compressors of the kind in question usually consist of a housing with an annular channel, called a side channel, located therein and having a semicircular cross-section for compressing a gas. The side channel is separated by a so-called interrupter between a gas inlet opening (suction side) and a gas outlet opening (pressure side). An impeller driven to rotate by an electric motor is located above the side channel. Viewed in the direction of rotation, multiple radially arranged blades are located on a pitch circle ring in the impeller, said blades dividing the pitch circle ring into corresponding cells, so-called blade chambers.

Gas, in particular air, enters into the side channel through the gas inlet opening, part of the gas molecules being swept along in a tangential direction by a blade. Because of the centrifugal force that is caused by the high speed of rotation of the impeller and acts on the considered gas molecules, the latter are accelerated radially outward, and, accelerated in this manner, they flow out of the blade and into the side channel. There, they are deflected in the direction of the impeller and are accelerated again by the next blade of the impeller so that the gas molecules move on a toroidally bent helical trajectory from the gas inlet opening to the gas outlet opening, the pressure in the gas rising continuously. The interrupter minimizes the amount of gas that is transported from the gas outlet opening to the gas inlet opening.

Since side channel compressors require no maintenance and owing to their oil-free compression operation, to their longevity and to the option of high pressure buildup, they are extremely well suited for use in devices for transnasal insufflation, so-called TNI devices, which are known from DE 10 2006 024 839 A1 or from DE 101 05 383 C2, for example.

Apart from the above-mentioned advantages of side channel compressors, they are, however, less effective in comparison to radial compressors because the highly turbulent flow in the side channel compressor converts a large portion of mechanical energy of the impeller into heat, which is useless as regards pressure, and because, owing to the structural shape of the impeller, air compressed in the impeller blades is dragged from the pressure side to the suction side, which also leads to diminished efficiency.

However, the main problem of the side channel compressors is the fact that there are extremely high noise emissions, which are caused on the one hand by the unsteady turbulent flow, which has a noise spectrum across the entire frequency range, and on the other hand by superimposed tonal sound components that are typical for side channels. The latter include vibrations of the housing and of the impeller due to imbalances, which correspond to the basic frequency and to a multiple of the basic frequency of the rotation of the impeller, and the so-called blade noise. Since the blade noise is caused by the pressure fluctuations at the interrupter inlet and outlet, which are induced by every single blade, the frequency of said noise corresponds to the rotation frequency of the impeller multiplied by the number of blades. Analogously to the harmonics of the basic frequency, the blade noise has sidebands at the distance of the rotation frequency. Being a high-frequency noise, the blade noise is especially disturbing.

STATE OF THE ART

Previous developments of side channel compressors of the kind in question are directed in particular at the elimination of the above-mentioned deficiencies.

For instance, DE 196 49 529 A1 discloses a side channel compressor in which a guide element is formed in the inlet-side end section of the side channel for the purpose of improving efficiency, said guide element allowing a more effective entrainment of the gas to be transported. From EP 1 703 136 B1, a side channel compressor having a complex side channel geometry including undercuts is known, in which an insert is used to improve the surface quality of the wall areas of the side channel so as to achieve a flow of the gas as free of turbulences as possible in order to thus improve efficiency. In the side channel compressor known from DE 199 13 950 A1, increased efficiency is achieved by continuously reducing the maximum channel depth in the direction of the outlet opening and by providing at least one section in which the side channel has a cross-section in the shape of a semi-ellipse, which leads to an increased volumetric flow and to increased compressor capacity. From DE 10 2006 041 557 A1, it is known to provide each blade of the impeller with a three-dimensional shape in such a manner that they produce a largely eddy-free, spatially twisted blade flow that is adjusted to the output to be generated. Other known side channel compressors deal with the reduction of the so-called axial and radial clearance in order to improve efficiency. Gas flows from the pressure side to the suction side through the rotation-induced gaps between the housing and the impeller, thereby reducing efficiency. While it is known from DE 20 2004 019 071 U1 to provide for this purpose a groove in the housing part or in the impeller, which groove is circumferential and oriented toward the sealing gap and in which a sealing ring made of an elastic material is inserted in a form-fitting manner, said sealing ring reaching into the sealing gap, DE 10 2005 040 305 A1 proposes realizing at least one of the opposing surfaces of the impeller and of the work chamber of the housing as a rough surface, whose roughness is preferably in the range of 53 to 45 μm.

Special measures for noise emission reduction are known from EP 2 207 967 B1, WO 2006/039894 A2 and U.S. Pat. No. 3,951,567. For instance, EP 2 207 967 B1 teaches providing, for the purpose of noise emission reduction, at least one flow recess in the free edge area of at least one impeller blade, said flow recess serving as a flow groove having a substantially rectangular cross-section, and that only 30% to 70% of all blades of the impeller are to be grooved so as to reduce gas turbulence structures. WO 2006/039894 A2 shows, apart from measures for clearance reduction by means of a spring washer/nut system or a tumble device, an impeller for a side channel compressor of the kind at hand, small intermediate blades for noise reduction being provided in the blade chambers. U.S. Pat. No. 3,951,567 discloses a side channel compressor that provides a non-uniform distribution of the blades on the impeller so as to reduce noise emissions.

In devices for flow therapy (e.g., known under the terms transnasal insufflation TNI, high flow therapy HFT, nasal high flow NHF, transnasal high flow THF), defined constant volumetric flows (gas flows) are required, which are only insufficiently produced by the currently known, above-listed low-noise side channel compressors because of their blade chamber architecture. At the same time, noise emission reduction has to be especially observed during generation of the volumetric flow because an anti-snoring device (DE 101 05 383 C2), for example, should not disturb the partner of the sleeper through compressor noises instead of snoring sounds.

Objective Problem and Solution

Hence, it is the object of the present invention to create a small, low-noise side channel compressor for producing a defined, constant volumetric flow (air/gas flow) for devices for ventilation therapy.

This object is attained by the side channel compressor specified in patent claim 1. Advantageous embodiments of the invention are the subject-matter of the dependent claims 2 to 10.

The side channel compressor according to present patent claim 1 is characterized in particular by the shape of its blade chambers and by the blade chamber walls (blades) that separate the blade chambers and become thicker toward the circumference of the impeller, their surfaces, which are oriented into the inside of adjacent blade chambers, extending parallel to the radially running center planes of said blade chambers. Apart from the advantage that each of the blade chambers can be completely produced in one work cycle, e.g. by means of a ball nose cutter, they promote in particular a more constant gas flow and facilitate noise reduction, as will be explained in the following paragraphs.

In the state of the art, the blades of the impeller have a constant wall thickness (cf., e.g., DE 196 49 529 A1). Consequently, the width of the blade chambers with growing radial distance to the axis of rotation of the impeller. Each blade chamber becomes wider towards the outside in the direction of the circumference of the impeller. Also, the bottom surfaces of the blade chambers are even in the direction of the circumference of the impeller. The incoming gas flows along the one blade toward the blade chamber bottom, then, deflected by 90°, along the blade chamber bottom, where it is again deflected by 90° and exits at the next blade away from the blade chamber bottom. Said flow has superimposed on it a radial flow from the radially inner side of the blade chamber toward the radially outer side of the blade chamber. Said radial flow is caused by the centrifugal forces that act on the gas molecules and lead to an increase in pressure at the radial outer wall of the blade chamber. Based on a compressible gas, the widening of the blade chamber in the circumferential direction causes a reduction in gas pressure because the gas expands so that an increase in pressure, which is possible because of the centrifugal force, is not entirely achieved if an equal number of entering and exiting molecules, i.e. mass particles, is assumed.

The invention avoids these two above-illustrated effects significantly by having the width of the blade chambers stay constant in the circumferential direction by means of the provided measures, consequently eliminating the expansion of the gas in the radial direction. Owing to the fabrication of the blade chambers using, e.g., a ball nose cutter, the chamber bottom is not even. The semicircular blade chamber bottom guides the air flowing in at the one blade toward the opposing blade, at which the gas exits, in a more continuous and consequently more favorable manner in terms of flow. In conclusion, a significantly less disturbed overall flow is achieved in this way, which results in a more constant flow of the gas volume at reduced noise generation. While efficiency is reduced because of the proposed blade chamber geometry in direct comparison to the geometries known from the state of the art because less space is available for the circulating flow, this disadvantage is compensated by further technical design features.

The other features indicated in dependent claims 2 and 6, according to which the blade chambers each have a bottom in the radial direction that has a semicircular cross-section and corresponds to the semicircular cross-section of the side channel, and according to which the transitions between the bottoms of the individual blade chambers and their blade chamber walls are provided with curves and the surfaces of the gas-conducting parts, in particular the side channel and the blade chambers, are designed to be hydraulically smooth, serve to increase efficiency based on the aforementioned improved flow properties. In this respect, it is to be noted that, e.g., the use of a ball nose cutter in the fabrication of an impeller is highly advantageous in comparison to the usually applied common casting technique because smooth surfaces are directly created, which do not require post-processing. By using, e.g., a ball nose cutter, the claimed curves are provided with the shape of a radius.

The high speed of rotation n of the impeller of about 30,000 rpm (dependent claim 5), which also causes the most noise, and at least 25, preferably 36 blade chambers realized on the impeller (dependent claim 4) lead to a blade noise of, for example, 18 kHz in case of 36 blade chambers, i.e. a noise outside of the human hearing range. Simultaneously to the shift of the noise into the inaudible range, the required diameter of the impeller is reduced by the quadratic dependence of the pressure on the speed of rotation; thus, the diameter of the impeller can be set to a diameter of about 50 mm, as has been done in the further embodiment of the invention in dependent claim 5. Owing to this measure, the structural space of, e.g., a TNI device into which a side channel compressor is to be integrated can be kept small, which offers a decisive advantage. Said advantage is aided by the impeller and the housing having at least one pitch circle (dependent claim 3).

To preclude undesired health-related side effects, the surfaces of the gas-conducting parts, in particular the side channel and the blade chambers, are designed to be anti-bacterial.

The clearance is reduced owing to the smooth surfaces of the housing mentioned in dependent claim 8 and to the impeller arranged thereon. Because of the further features also indicated in dependent claim 8, stating that an expansion section of the compressed gas is provided at the end of the interrupter, a gentle expansion of the gas is possible so that the speed of the gas can be converted into pressure at little loss, similar to the known principle of a diffuser. Both measures thus also serve to increase efficiency.

The design of the side channel compressor claimed in dependent claim 9 providing that sound absorbers can be connected at the gas inlet opening and/or at the gas outlet opening offers the option of additionally connecting known sound absorbers working according to the principle of a Helmholtz resonator or connecting circular sound absorbers if needed so as to avoid remaining noise emissions.

The use of materials of low density and at the same time of high strength as claimed in claim 10 serves, in the case of the impeller, to achieve low centrifugal forces at high speeds of rotation and to avoid disturbing noises in case of potential unbalances. These materials include, e.g., aluminum, magnesium and PEEK.

The use of the side channel compressor according to the invention in devices for ventilation therapy is claimed as well (claim 11).

EXEMPLARY EMBODIMENT

In the following paragraphs, a preferred embodiment of the invention will be explained in more detail with reference to the accompanying drawings. In the figures.

Figure 1:
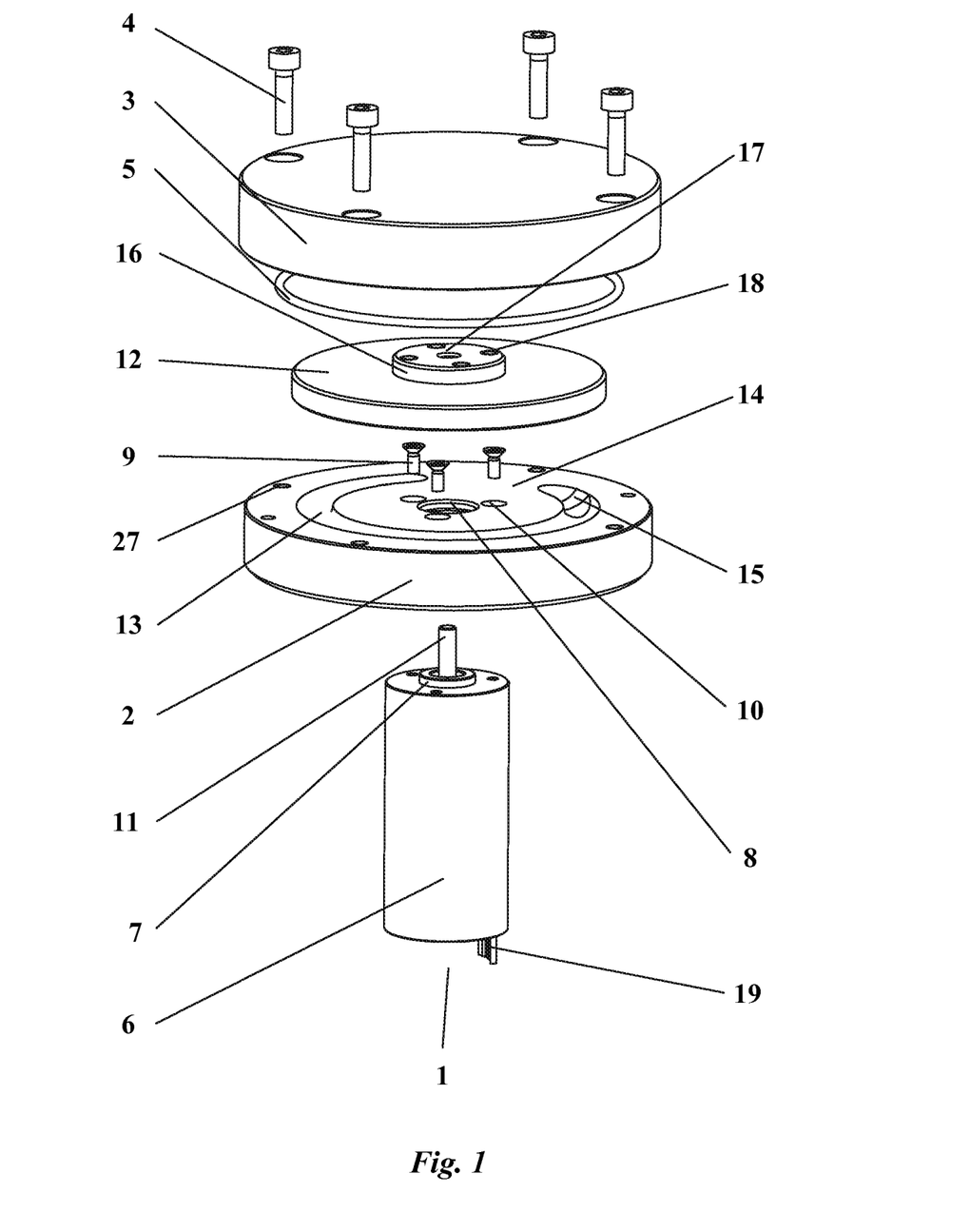
FIG. 1 shows a side channel compressor in a total illustration

FIG. 1 illustrates the side channel compressor (1) in an exploded illustration. A housing lid (3) is screwed to a housing (2) by means of cylinder head screws (4). A toroidal ring (5) or O-ring seals the housing lid (3) against the housing (2). An electric motor (6) is secured with its centering shoulder (7) in a centering bore (8) of the housing (2) by means of countersunk head screws (9) that penetrate counterbores (10) and, by means of its motor pin (11), rotates the impeller (12) that is secured thereon. In the housing (2), a side channel (13) including the limiting interrupter (14) and the expansion section (15) is visible. The impeller (12) has a centering shoulder (16), a bore (17) and threaded bores (18). The number 19 designates the electrical connection for the electric motor (6).

Figure 2:
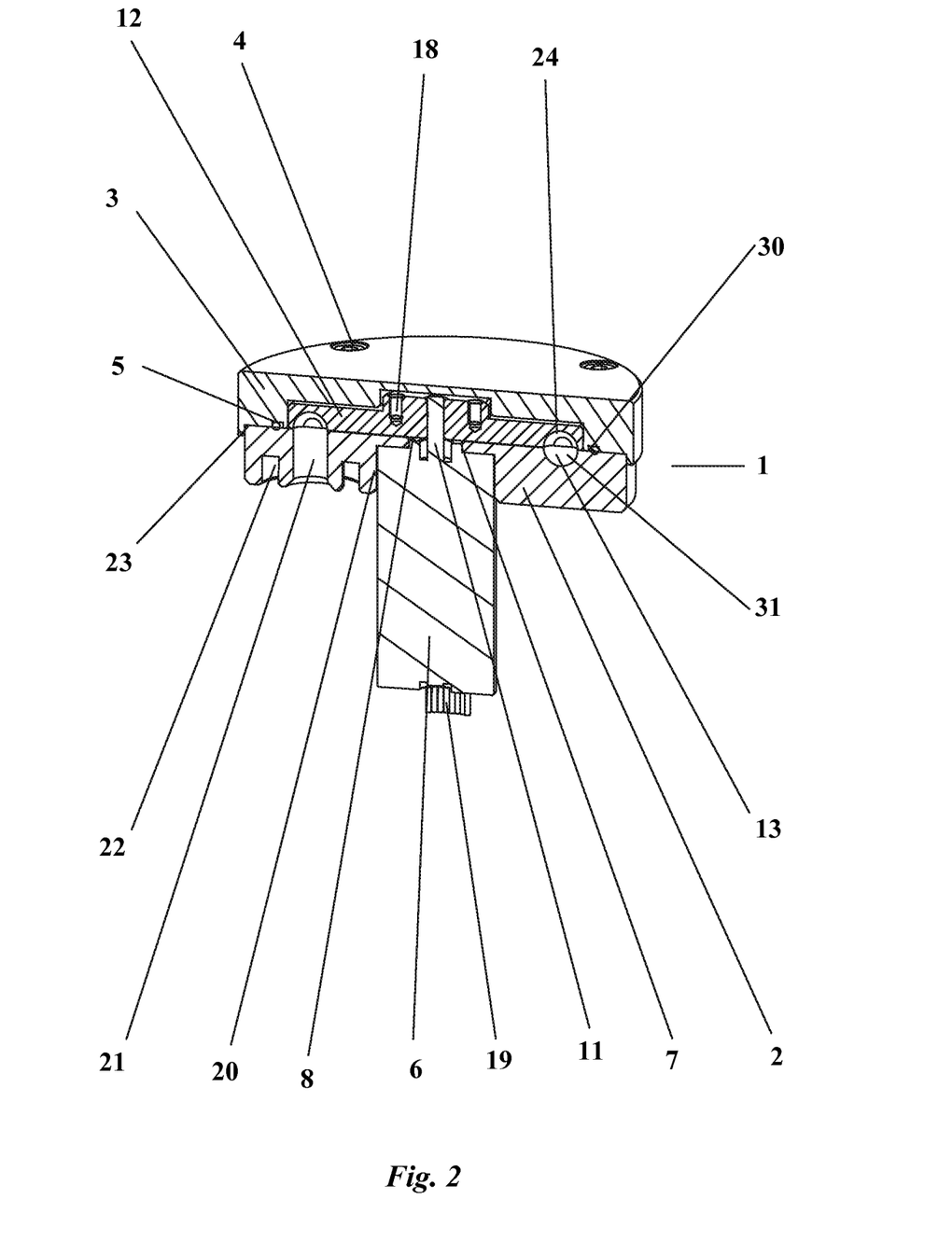
FIG. 2 shows a side channel compressor in a cross-section

FIG. 2 shows a section through the side channel compressor (1) in the mounted state. The electric motor (6) with its centering shoulder (7) sits in the housing (2) comprising a countersink (20) and the centering bore (8). The electrical connection (19) for its operation is located at the opposite end of the electric motor (6). The section also shows a gas inlet opening (21) and an annular groove (22) surrounding the same. The side channel (13) having a semicircular cross-section (31) is incorporated within the housing (2). The housing lid (3) is centered on the housing (2) by means of a recess (23) and is screwed thereto by means of cylinder head screws (4). Additionally, the threaded bores (18) are illustrated. The housing lid (13) is sealed against the housing (2) by the toroidal ring (5), that is inserted into an annular groove (30). Also, the blade chambers (24) in the impeller (12) are shown, which are cut in the radial plane, said blade chambers (24) being located opposite of the side channel (13) and of the gas inlet opening (21). The impeller (12) is secured onto the motor pin (11).

Figure 3:
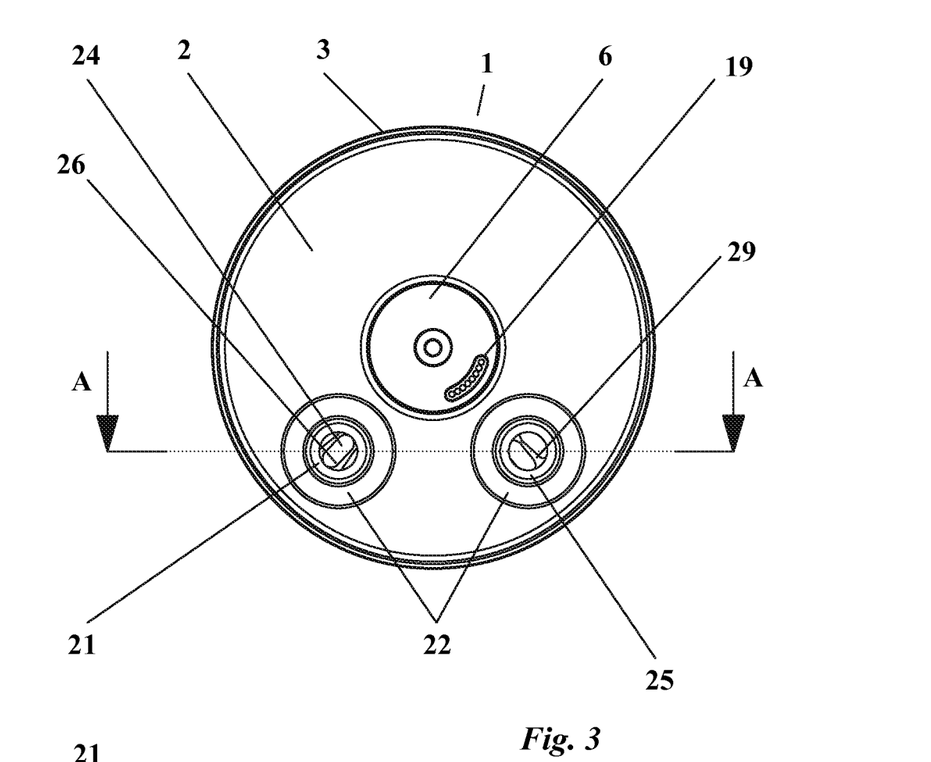
FIG. 3 shows the connection side of the side channel compressor

FIG. 3 shows the connection side of the side channel compressor (1) comprising the electric motor (6), the connection (19), the housing lid (3), the housing (2) and a gas inlet opening (21) and a gas outlet opening (25) including the surrounding annular grooves (22). A blade chamber (24) and a blade (26) are additionally illustrated in the gas inlet opening (21), and a blade chamber wall (29) having a width becoming thicker toward the circumference of the impeller is illustrated in the gas outlet opening (25).

Figure 4:
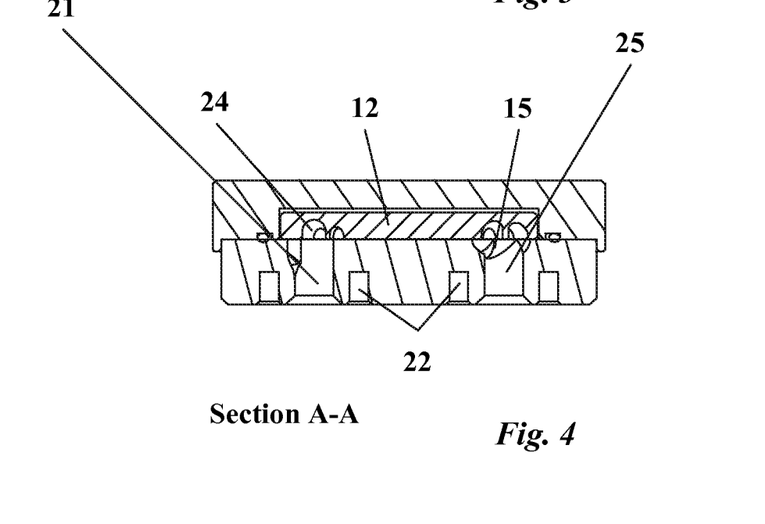
FIG. 4 shows a section A-A through the gas inlet and gas outlet openings

FIG. 4 shows a section A-A through the gas inlet and gas outlet openings (21, 25) of the side channel compressor (1). The side channel (13) including the expansion section (15) begins and ends therein, respectively. In turn, the gas inlet and gas outlet openings (21, 25) end in the blade chambers (24) within the impeller (12).

Figure 5:
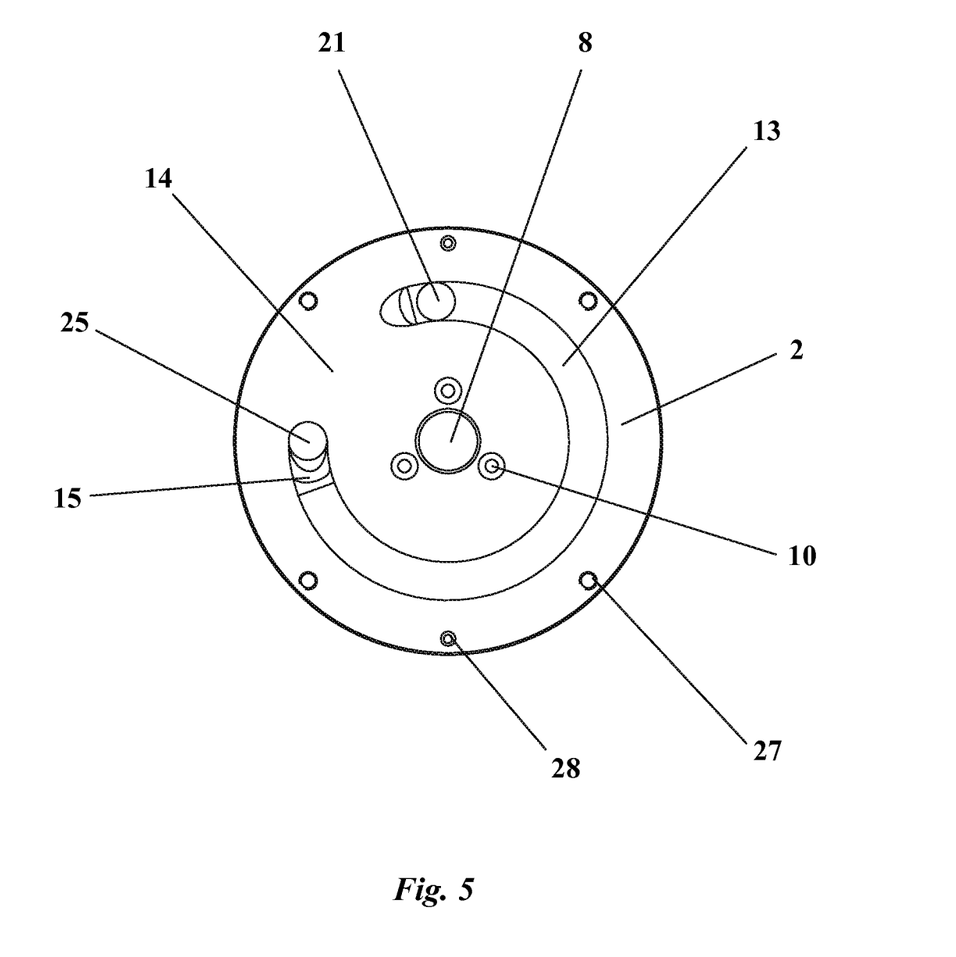
FIG. 5 shows a lid-side view of the housing

FIG. 5 shows the view onto the housing (2) from the side onto which the housing lid (3) is screwed. The side channel (13) begins at the gas inlet opening (21) and ends at the gas outlet opening (25), the side channel (13) having a center angle of approximately 270°. The interrupter (14) is located between the ends of the side channel (13). Furthermore, the centering bore (8) for receiving the centering shoulder (7) for the electric motor (6) is shown. The number (10) designates the counterbores for fixing the electric motor (6) by screws. Four threaded bores (27) serve to fix the housing lid (3) by screws. The threaded bores (28) allow the side channel compressor (1) to be fixed as a whole by means of screws. The expansion section (15) forms the passage from the side channel (13) to the gas outlet opening (25).

Figure 6:
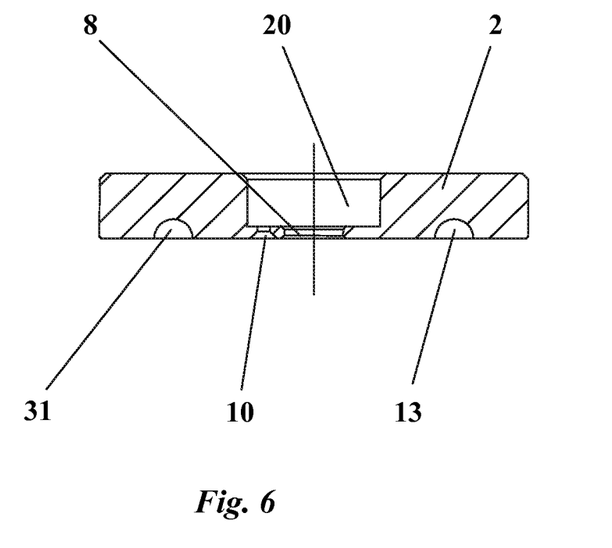
FIG. 6 shows a full section through the housing

FIG. 6 illustrates a full section through the housing (2). The centering bore (8) is adjacent in the axial direction to the countersink (20) for receiving the electric motor (6), said centering bore (8) being penetrated by the motor pin (11). The counterbore (10) receives countersunk screws (9) for securing the electric motor (6). Also, the semicircular cross-section (31) of the side channel (13) is illustrated.

Figure 7:
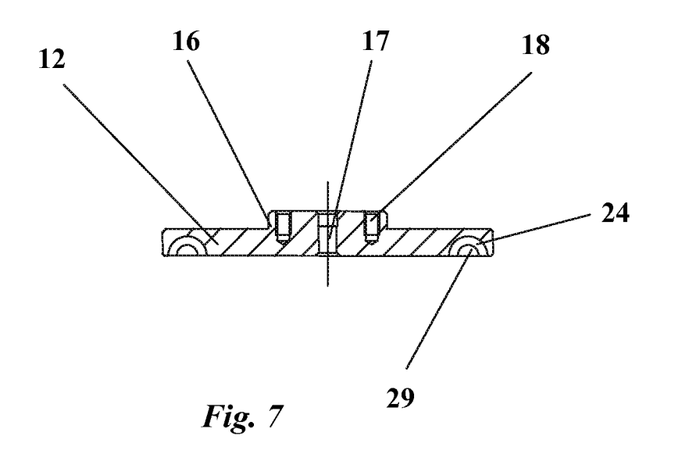
FIG. 7 shows a full section through the impeller

FIG. 7 shows the impeller (12) in a full section including the bore (17) for receiving the motor pin (11) of the electric motor (6). The semicircular blade chamber (24) is illustrated without distortion in the radial section plane. Also, a plane blade chamber wall (29) is indicated by means of the smaller semicircle. The shown semicircular ring, limited at the inside by the blade chamber wall (29) and at the outside by the contour of the blade chamber (24), has a width that is equal to the radius of the ball nose cutter with which the blade chamber (24) is cut. Furthermore, note is to be taken of the centering shoulder (16) and the threaded bores (18).

Figure 8:
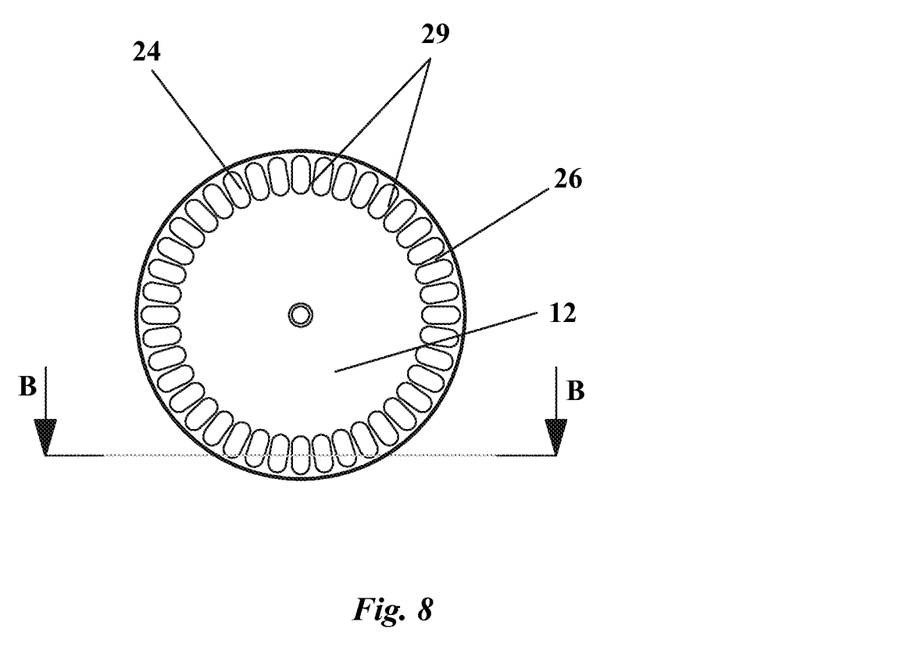
FIG. 8 shows a view of the impeller

An axial view of the impeller (12) including the blade chambers (24) and the blades (26) is illustrated in FIG. 8. In the embodiment example, 40 blade chambers (24) are present whose radial extension is equal. The shape and size of the ball nose cutter determines the constant width of the blade chamber (24), thus producing planar blade chamber walls (29) that extend parallel to the radially running center plane of the blade chambers (24). Owing to the constant width of the blade chambers (24), the blades do not become wider to the outside in the radial direction. As a result of this design, each blade chamber (24) has the same chamber volume.

Figure 9:
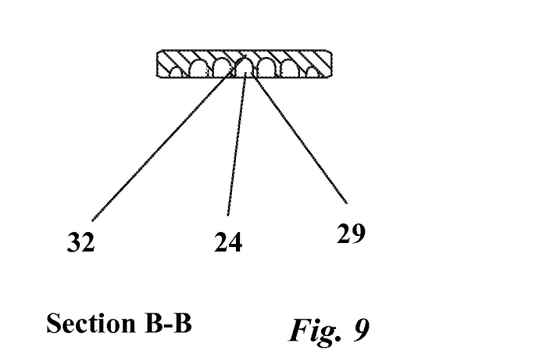
FIG. 9 shows a section B-B through the impeller

Section B-B through the impeller (12) in FIG. 9 shows the semicircular bottom (32) of the blade chamber (24). The curve, in this case the radius of said bottom, is determined by the radius of the ball nose cutter. The planar blade chamber wall (29) is visible as well. All blade chambers (24) penetrate the impeller (12) to the same depth. Alternatively to the production by means of a ball nose cutter, an erosion process can be applied as well.

An impeller diameter of 50 mm has proven particularly advantageous for some applications. Materials of low density and at the same time of high strength are suitable to achieve low centrifugal forces at high speeds of rotation. The surfaces that come into contact with the gas are designed to be hydraulically smooth and antibacterial.

In operation, the electric motor (6) rotates the impeller (12), gas being sucked into the side channel (13) via the gas inlet opening (21). This effect is caused by the blade chambers (24), into which the gas molecules enter coming from the gas inlet opening (21). The gas molecules are radially and tangentially accelerated, as is the case in any circular motion. This causes multiple flow components to be superimposed. On the one hand, the gas molecules are accelerated radially outward because of the occurring centrifugal force and increase the pressure in the outer area of the blade chamber (24). The compressed gas enters the side channel (13) and is deflected on a circular path following the wall so as to again enter a subsequent blade chamber (24). On the other hand, the gas molecules flow along the one blade (26) in an axial direction with respect to the axis of rotation of the electric motor (6) and are deflected by the semicircular bottom (32) of the blade chamber (24) so as to be subsequently pressed into the side channel (13) in the opposite direction by the opposite blade (26). This, too, leads to an increase in pressure. As a result, a helical flow is generated, the gas pressure constantly increasing until the gas exits at the gas outlet opening (25). The interrupter (14), which almost entirely prevents the gas from flowing in the circumferential direction, serves this purpose, too. Only the residual gas volume remaining in the blade chambers (24) is transported further at the interrupter (14) by the impeller (12).

LIST OF REFERENCE SIGNS 1 side channel compressor
2 housing
3 housing lid
4 cylinder head screw
5 toroidal ring
6 electric motor
7 centering shoulder
8 centering bore
9 countersunk head screw
10 counterbore
11 motor pin
12 impeller
13 side channel
14 interrupter
15 expansion section
16 centering shoulder
17 bore
18 threaded bore
19 connection
20 countersink
21 gas inlet opening
22 annual groove
23 recess
24 blade chamber
25 gas outlet opening
26 blade
27 threaded bore for screw 4
28 threaded bore for securing the side channel compressor 1
29 blade chamber wall
30 annular groove
31 cross-section of the side channel 13
32 bottom

The invention claimed is:

1. A small, low-noise side channel compressor for providing breathing fluid via devices for ventilation therapy, the side channel compressor comprising:
a housing;
an annular side channel located within the housing and having a cross-section for compressing a gas;
a disk-shaped impeller driven to rotate by an electric motor and having a plurality of blade chambers that are located on a shared pitch circle, are arranged opposite of the side channel and are distributed across the pitch circle, the blade chambers being formed by blade chamber walls and a bottom;
a gas inlet opening formed in the housing and being in fluid communication with the side channel for introducing a gas to be compressed;
a gas outlet opening formed in the housing and being in fluid communication with the side channel for discharging the compressed gas from the side channel;
an interrupter located in the side channel between the gas outlet opening and the gas inlet opening, wherein the blade chamber walls, separating the individual blade chambers, become thicker toward the circumference of the impeller in such a manner that blade chamber surfaces, oriented into the inside of adjacent blade chambers, extend parallel to radially running center planes of said blade chambers, wherein in the radial direction, each of the blade chambers has a bottom that follows a curve in the cross-section, and the transitions between the bottoms of the individual blade chambers and their blade chamber walls are provided with curves, wherein at least surfaces of the side channel and the blade chambers are hydraulically smooth, each of the blade chambers having at least one end portion with an arcuate portion extending in a circumferential direction of the housing, wherein the arcuate portions of the blade chambers are identical, each blade chamber having a longitudinal axis and each blade chamber being mirror symmetrical with respect to the longitudinal axis thereof.

2. The small, low-noise side channel compressor according to claim 1, wherein the impeller and the housing each have at least one pitch circle, wherein a shape of each of the blade chambers is identical to a shape of another one of the blade chambers, each of the blade chambers having a transverse axis perpendicular to the longitudinal axis, each blade chamber being mirror symmetrical with respect to the transverse axis.

3. The small, low-noise side channel compressor according to claim 1, wherein at least 25 blade chambers are realized in the impeller, wherein the blade chambers have a shape identical to each other.

4. The small, low-noise side channel compressor according to claim 1, wherein the diameter of the impeller is about 50 mm and the speed of rotation n of the impeller is about 30,000 rpm.

5. The small, low-noise side channel compressor according to claim 1, wherein the surfaces of the gas-conducting parts, in particular the side channel and the blade chambers, are designed to be antibacterial, each of the blade chambers having another end portion with an another arcuate portion extending in the circumferential direction of the housing.

6. The small, low-noise side channel compressor according to claim 1, wherein the housing and the impeller have smooth surfaces, and an expansion section of the compressed gas is provided at the end of the interrupter.

7. The small, low-noise side channel compressor according to claim 1, wherein additional sound absorbers are connected at the gas inlet opening and/or at the gas outlet opening.

8. The small, low-noise side channel compressor according to claim 1, wherein materials of low density and at the same time of high strength are used in the impeller.

9. The small, low-noise side channel compressor according to claim 1, wherein each of the blade chambers has a blade chamber width, the blade chamber width being constant in a direction of an outer circumferential surface of the impeller.

10. A device for ventilation therapy, comprising:
built in the device for providing breathing fluid for ventilation therapy, a side channel compressor comprising:
a housing;
an annular side channel located within the housing and having a cross-section for compressing a gas;

a disk-shaped impeller driven to rotate by an electric motor and having a plurality of blade chambers that are located on a shared pitch circle, are arranged opposite of the side channel and are distributed across the pitch circle, the blade chambers being formed by blade chamber walls and a bottom;

a gas inlet opening formed in the housing and being in fluid communication with the side channel for introducing a gas to be compressed;

a gas outlet opening formed in the housing and being in fluid communication with the side channel for discharging the compressed gas from the side channel; and an interrupter located in the side channel between the gas outlet opening and the gas inlet opening, wherein the blade chamber walls, separating the individual blade chambers, become thicker toward the circumference of the impeller in such a manner that blade chamber surfaces, oriented into the inside of adjacent blade chambers, extend parallel to radially running center planes of said blade chambers, wherein in the radial direction, each of the blade chambers has a bottom that follows a curve in the cross-section, and the transitions between the bottoms of the individual blade chambers and their blade chamber walls are provided with curves, wherein at least surfaces of the side channel and the blade chambers, are hydraulically smooth, each of the blade chambers having at first end portion with a first arcuate portion extending in a circumferential direction of the housing and a second end portion with a second arcuate portion extending in the circumferential direction of the housing, wherein the first arcuate portion is identical to the second arcuate portion, each of the blade chambers being mirror symmetrical with respect to a longitudinal axis thereof.

11. A device according to claim 10, wherein the impeller and the housing each have at least one pitch circle, each of the blade chambers having an identical shape, each of the blade chamber being mirror symmetrical with respect to a transverse axis thereof, the transverse axis being perpendicular to the longitudinal axis.

12. A device according to claim 10, wherein at least 25 blade chambers are realized in the impeller, each of the blade chambers having a shape identical to one another.

13. A device according to claim 10, wherein the diameter of the impeller is about 50 mm and the speed of rotation n of the impeller is about 30,000 rpm.

14. A device according to claim 10, wherein the surfaces of the side channel and the blade chambers are designed to be antibacterial, each of the blade chambers having an identical shape.

15. A device according to claim 10, wherein the housing and the impeller have smooth surfaces, and an expansion section of the compressed gas is provided at the end of the interrupter.

16. A device according to claim 10, wherein sound absorbers are connected at the gas inlet opening and/or at the gas outlet opening.

17. A device according to claim 10, wherein materials of low density and at the same time of high strength are used in the impeller.

18. A device according to claim 10, wherein each of the blade chambers has a blade chamber width, the blade chamber width being constant in a direction of an outer circumferential surface of the impeller.

19. A small, low-noise side channel compressor for devices for ventilation therapy, the side channel compressor comprising:

a housing;

an annular side channel located within the housing and having a cross-section for compressing a gas;

a disk-shaped impeller comprising a rotational axis, the impeller being driven to rotate by an electric motor about the rotational axis and the impeller having a plurality of blade chambers that are located on a shared pitch circle, are arranged opposite of the side channel and are distributed across the pitch circle, the blade chambers being formed by blade chamber walls and a bottom portion of the impeller;

a gas inlet opening formed in the housing, the gas inlet opening being in fluid communication with the side channel for introducing a gas to be compressed;

a gas outlet opening formed in the housing, the gas outlet opening being in fluid communication with the side channel for discharging the compressed gas from the side channel for delivering breathing fluid to the devices for ventilation therapy;

an interrupter located in the side channel between the gas outlet opening and the gas inlet opening, wherein the blade chamber walls, separating the individual blade chambers, become thicker toward the circumference of the impeller in such a manner that blade chamber surfaces, oriented into the inside of adjacent blade chambers, extend parallel to radially running center planes of said blade chambers, each of the blade chambers comprising a first end portion and a second end portion, the first end portion being located radially inward of the second end portion with respect to the rotational axis, the first end portion comprising a first end portion width, the second end portion comprising a second end portion width, the first end portion width being equal to the second end portion width, each of the first end portion and the second end portion comprising an arcuate portion extending in a circumferential direction of the housing, the arcuate portion of the first end portion having a first arcuate contour, the arcuate portion of the second end portion having a second arcuate contour, the first arcuate contour being identical to the second arcuate contour, each of the blade chambers being mirror symmetrical with respect to a respective longitudinal blade chamber axis.

20. A small, low-noise side channel compressor according to claim 19, wherein in a radial direction, each of the blade chambers has a bottom that follows a curve in the cross-section, and the transitions between the bottoms of the individual blade chambers and the blade chamber walls associated with the individual blade chambers are provided with curves, at least surfaces of the side channel and the blade chambers being hydraulically smooth, each of the blade chambers having a blade chamber width defined between the first end portion and the second end portion, the blade chamber width being constant in the radial direction of an outer circumferential surface of the impeller with respect to the rotational axis, the blade chamber width being equal to the first end portion width and the second end portion width, each of the blade chambers having an identical shape, each of the blade chambers comprising being mirror symmetrical with respect to a transverse axis, the transverse axis being perpendicular to the longitudinal axis.

* * * * *